United States Patent [19]
Fujieda

[11] Patent Number: 5,500,697
[45] Date of Patent: Mar. 19, 1996

[54] OPHTHALMIC APPARATUS FOR MEASURING REFRACTIVE CHARACTERISTIC OF EYE TO BE MEASURED

[75] Inventor: Masanao Fujieda, Toyohashi, Japan

[73] Assignee: Nidek Co., Ltd., Japan

[21] Appl. No.: 280,192

[22] Filed: Jul. 25, 1994

[30] Foreign Application Priority Data

| Jul. 30, 1993 | [JP] | Japan | ................................ 5-208434 |
| Oct. 29, 1993 | [JP] | Japan | ................................ 5-294407 |

[51] Int. Cl.$^6$ ................................................. A61B 3/10
[52] U.S. Cl. ........................ 351/212; 351/211; 351/247
[58] Field of Search .................................. 351/211, 212, 351/206, 247, 221, 205

[56] References Cited

U.S. PATENT DOCUMENTS

| 4,859,051 | 8/1989 | Fukuma et al. | ........................ 351/211 |
| 5,214,456 | 5/1993 | Gersten | ................................ 351/212 |
| 5,309,186 | 5/1994 | Mizuno | ................................. 351/211 |
| 5,357,294 | 10/1994 | Shimizu et al. | ........................ 351/212 |

FOREIGN PATENT DOCUMENTS 58-75528   5/1983   Japan.

*Primary Examiner*—William L. Sikes
*Assistant Examiner*—Hung Xuan Dang
*Attorney, Agent, or Firm*—Parkhurst, Wendel & Rossi

[57] ABSTRACT

An ophthalmic apparatus measures characteristics of an eye using a projection mechanism that projects a target onto a fundus of the eye in a plurality of meridional directions in a cornea of the eye so as to substantially cover all over the cornea. A detection mechanism detects a position of the target image projected onto the fundus. A processor calculates refractive power values in the meridional directions based on the positions detected by the detection mechanism. The results are graphically displayed to permit an operator to quickly understand and interpret the results at a glance.

14 Claims, 16 Drawing Sheets

5,500,697

OPHTHALMIC APPARATUS FOR MEASURING REFRACTIVE CHARACTERISTIC OF EYE TO BE MEASURED

BACKGROUND OF THE INVENTION

1. Field of the Invention

The present invention relates to an ophthalmic apparatus for measuring refractive characteristic of an eye to be measured and in particular, to an ophthalmic apparatus for measuring eye refractive power in a plurality of meridional directions of the eye to be measured and cornea shape based on curvature distribution in a cornea of the eye.

2. Description of Related Art

Conventionally, as an ophthalmic apparatus for measuring refractive power of an eye to be measured, it is well-known an apparatus through which refractive power is measured by projecting a measuring target onto a fundus of the eye to be measured and detecting an image of the target projected onto the fundus. Such kind of the apparatus has a purpose to prescribe glass lens or contactlens, therefore the apparatus is comprised so as to be able to determine three values such as the spherical refractive power, the cylindrical refractive power and the cylindrical axial angle, these values being necessary for correctly preparing the glass lens or the contactlens. That is to say, in the detecting optical system of the above apparatus, it is adopted, for instance, a method in which two measuring luminous fluxes are projected to positions symmetrical about the visual axis of the measured eye or a method in which one luminous flux is projected to the center of the pupil in the eye and the reflected luminous flux from the fundus is introduced through three openings which are arranged at positions conjugated with the cornea of the eye, thereby diffusion of the luminous flux to three meridional direction is detected.

The refractive power of the spherical surface, the cylindrical surface and the astigmatism axial angle measured through the above apparatus are obtained by treating the measured data in the meridional directions through the equation $\sin 2\theta$.

Even in the conventional apparatus, it can obtain the necessary and sufficient results so long as the apparatus has the purpose for prescribing glass lens or contactlens. Here, the measurement of the eye is conducted in the apparatus based on the assumption that an eyeball is symmetrical. However, as a matter of fact, it is generally said that more than ⅓ of men or women who have refractive ametropy, have asymmetrical astigmatism. Thus, in the conventional apparatus, since the mean refractive power of the eye is measured in neglecting the above point, it is not enough at a point that the correct distribution of the refractive power in the eye cannot be measured.

Further, it is recently known an ophthalmic treatment in which the surface of the cornea is ablated or incised by excimer laser, thereby the curvature of the cornea is changed and refractive ametropy can be corrected. In the ophthalmic treatment, the operation has to be conducted based on the correct data of the refractive power of the eye to be operated and it is necessary the detailed data thereof to observe the status of the operated eye after the operation. However, in the above conventional apparatus, it cannot be obtained sufficient data of the refractive power of the eye which is necessary for the above operation.

And in case that the above ophthalmic treatment is conducted, at first, it is necessary to know both the detailed data of the cornea shape and the refractive power value of the eye to be operated.

Here, as the apparatus through which the cornea shape data can be obtained in detail, it is conventionally known an apparatus utilizing so-called Cornea Topography through which the curvature distribution of the cornea can be measured over a wide range thereof and the measured distribution can be visualized. In such the apparatus, the curvature distribution of the cornea is visualized as follows. That is, a reflected image of the cornea according to Placido-Ring projected onto the eye to be measured is photographed by a CCD camera and a Placido-Ring image is detected by conducting picture processing. Further, the curvature distribution over substantially entire range of the cornea of the eye is obtained by conducting calculation processing in which positional data of the Placido-Ring image located at a predetermined position is processed through a well-known manner and thereafter the curvature distribution is graphically visualized on a T.V monitor. In the apparatus that graphic display is done, it is also known an apparatus in which graphic display on T.V. monitor is conducted through color graphic so that the curvature distribution of the cornea can be easily understood.

And when the ophthalmic treatment mentioned above is conducted, it has to be used two kinds of the apparatuses, one being the apparatus utilizing Cornea Topography for measuring the cornea shape and the other being the apparatus for measuring the refractive power value, in order to obtain both the cornea shape data and the refractive power value of the eye to be operated before the operation.

However, if the two apparatuses are necessary to prepare, there is a problem that not only equipment investment is increased but also wide space for equipping the apparatuses has to be secured. And there is also a problem that an inspector has to move between the apparatuses while measuring. Further, data processing of the data obtained from the two apparatuses is very troublesome, thus the measurement efficiency becomes worse.

SUMMARY OF THE INVENTION

Accordingly, it is an object of the present invention to overcome the above mentioned problems and to provide an ophthalmic apparatus for measuring characteristic of an eye to be measured comprising;

projection means for projecting a target onto a fundus of the eye in a plurality of meridional directions in a cornea of the eye so as to substantially cover all over the cornea;

detection means for detecting a position of a target image projected onto the fundus by the projection means;

calculation means for calculating refractive power values in the meridional directions based on a detected result through the detection means; and display means for graphically displaying distribution of the refractive power values calculated by the calculation means.

According to the ophthalmic apparatus, the refractive power in each of the meridional direction of the eye can be correctly measured, therefore the refractive power data obtained by the above apparatus can be suitably utilized in the various ophthalmic operations.

And according to another aspect of the present invention, it is provided an ophthalmic apparatus for measuring characteristic of an eye to be measured, the ophthalmic apparatus comprising:

position adjusting means for aligning an optical system in the apparatus in a predetermined relationship against the eye;

first projection means for projecting a first target having a plurality of ring patterns onto a cornea of the eye so as to measure a cornea shape;

first pick up means for picking up the first target projected by the first projection means;

image process means for extracting an image of the first target by processing a first target picked up through the first pick up means;

cornea shape calculation means for calculating the cornea shape based on a position of the image of the first target;

second projection means for projecting a second target onto a fundus of the eye in a plurality of meridional directions so as to measure refractive power values;

light detection means for detecting a second target image projected by the second projection means;

refractive power calculation means for calculating the refractive power values based on a detected result through the light detection means;

mode exchanging means for exchanging a cornea shape measurement mode and a refractive power measurement mode; and display means for displaying the measured cornea shape and the measured refractive power.

According to the above apparatus, the curvature distribution of the cornea and the eye refractive power can be easily measured, therefore not only data processing of the curvature distribution data and the eye refractive power data can be easily conducted but also the measurement efficiency can be made better, without increasing equipment investment and equipping wide space.

The above and further objects and novel features of the invention will more fully appear from the following detailed description when the same is read in connection with the accompanying drawings. It is to be expressly understood, however, that the drawings are for purpose of illustration only and not intended as a definition of the limits of the invention.

BRIEF DESCRIPTION OF THE DRAWINGS

The invention will be described with reference to the following drawings, wherein.

DETAILED DESCRIPTION OF THE PREFERRED EMBODIMENTS

A detailed description of the preferred embodiments according to the present invention will now be given referring to the accompanying drawings. First, the first embodiment of an ophthalmic apparatus for precisely measuring a refractive power of an eye to be measured will be described. Here, in the apparatus, though various optical systems such as the observing optical system, the alignment optical system, the projecting optical system for fixation target and the like are arranged, each optical system will be explained in the fourth embodiment hereinafter.

Figure 1:
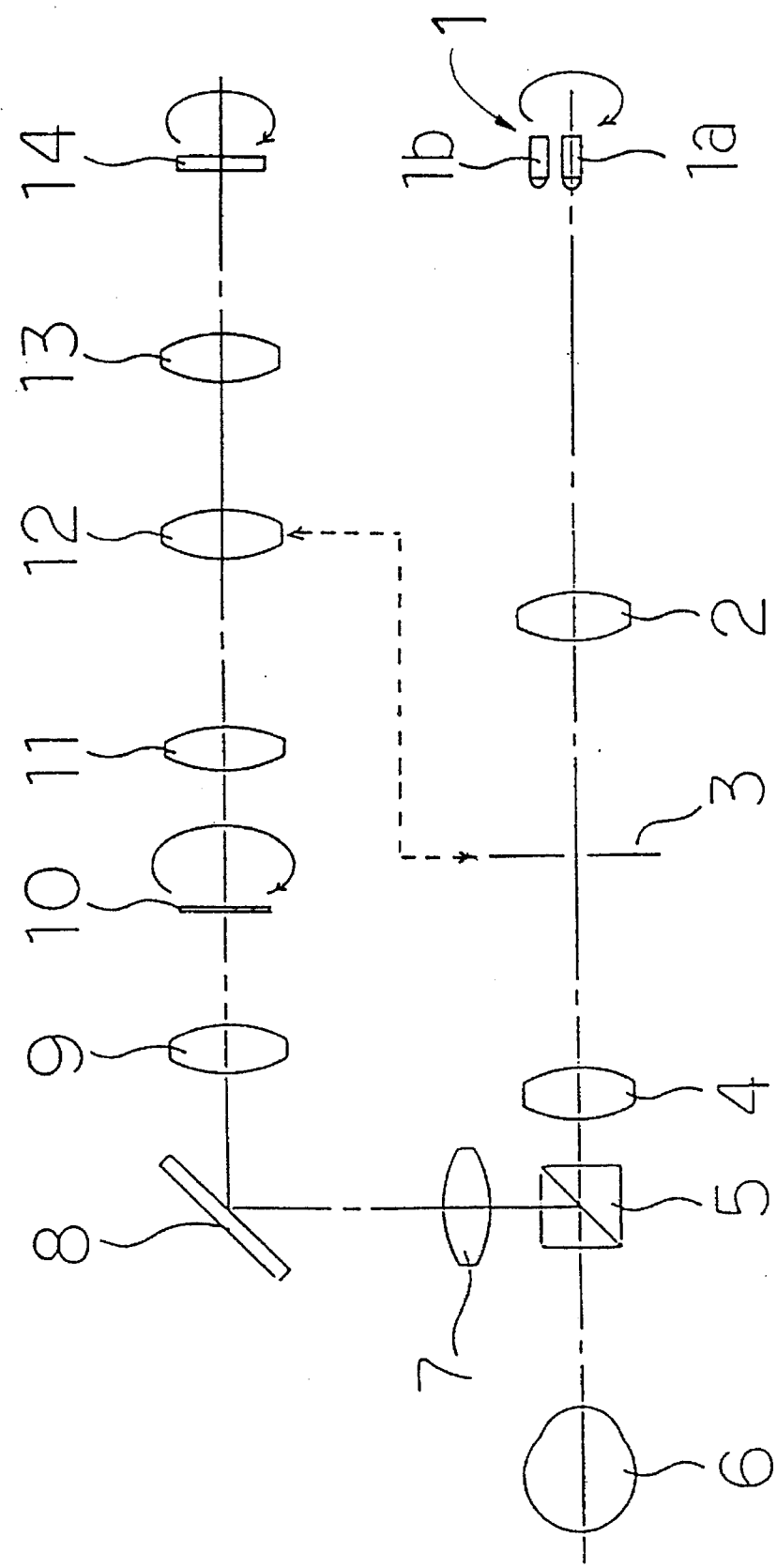
FIG. 1 is a schematic view of the optical system in the first embodiment according to the present invention.
Figure 2:
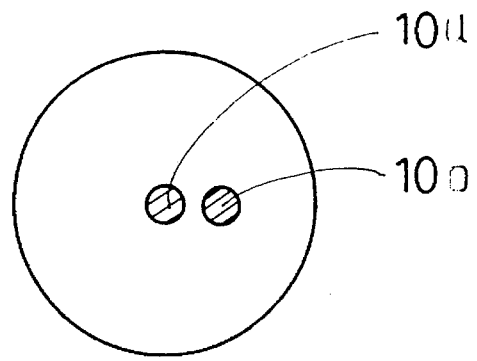
FIG. 2 is a view to explain a cornea reflecting rejection mask arranged in the optical system of the first embodiment.

In FIG. 1, numeral 1 indicates two light sources (1a and 1b) each of which emits rays with a wavelength in an infrared region. The light source 1a is arranged on a optical axis and the light source 1b is arranged distant from the optical axis. The light source 1b is arranged so that it can rotate around the optical axis. Numeral 2 is a condenser lens and the light sources 1a, 1b are positioned at a front focal point of the condenser lens 2 existing at the side of the light sources 1a, 1b. Numeral 3 is a spot diaphragm which is arranged so as to be movable to a position conjugated with the fundus of an eye 6 to be examined. Numeral 4 indicates an objective lens and numeral 5 indicates a beam splitter. And numeral 7 is an objective lens, numeral 8 is a reflecting mirror and numeral 9, 11 are relay lenses. Numeral 10 indicates a cornea reflecting rejection mask which is arranged at a position conjugated with the cornea of the eye 6 and, as shown in FIG. 2, the cornea reflecting rejection mask 10 has two light shading portions 10a and 10b which shade the reflecting light from the cornea corresponding to the light sources 1a, 1b, respectively. Numeral 12 indicates a movable lens which is moved synchronous with the spot diaphragm 3 and numeral 13 indicates an imaging lens. And numeral 14 indicates a light receiving device for measurement which is arranged so as to be rotatable around the optical axis synchronous with both the light source 1b and the cornea reflecting rejection mask 10.

Figure 3:
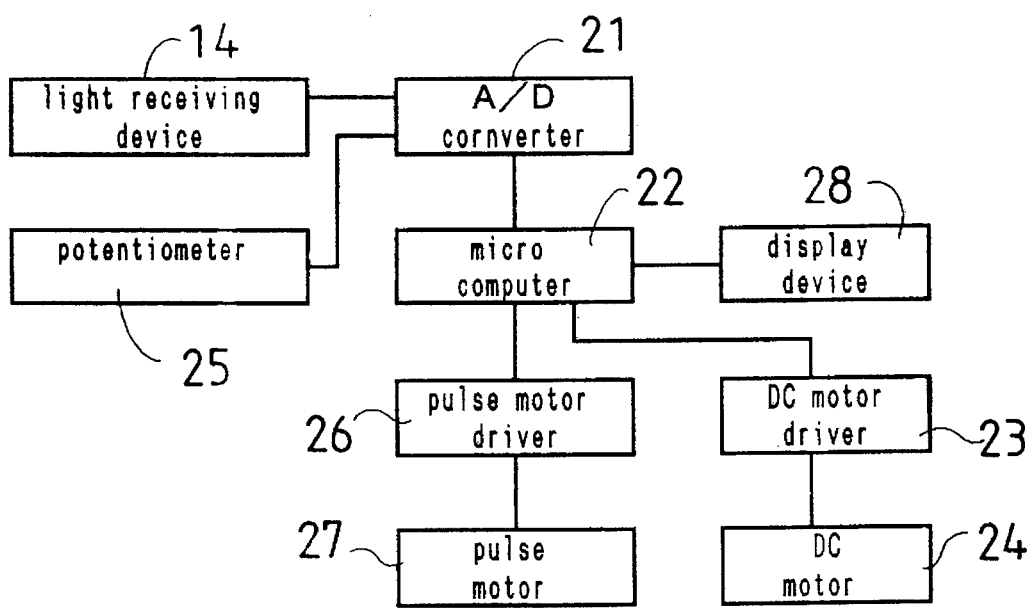
FIG. 3 is an electric block diagram of the first embodiment.

Next, electric block diagram will be described with reference to FIG. 3. In FIG. 3, the light signal received by the light receiving device 14 is output to an A/D converter 21 and converted into digital signal through the A/D converter 21. The converted digital signal is input to a microcomputer 22. The microcomputer 22 controls a DC motor driver 23 and a DC motor 24 so that the spot diaphragm 3 is conjugated with the fundus of the eye 6 based on the light signal received by the light receiving device 14, thereby the movable lens 12 and the spot diaphragm 3 are moved along the optical axis. A potentiometer 25 detects a voltage value corresponding to the position of the spot diaphragm 3 when the spot diaphragm 3 is moved by the DC motor 24. The detected signal (voltage value) is input to the microcomputer 22 after being converted into the digital signal by the A/D converter 21. Thereby, the spherical refractive power of the eye in the meridional direction is calculated by the microcomputer 22. Numeral 26 indicates a pulse motor driver and numeral 27 indicates a pulse motor through which the light source 1b, the cornea reflecting rejection mask 10 and the light receiving device 14 are rotated, thereby the axial angles thereof are changed. Numeral 28 is a display device on which the measured result is displayed under control by the microcomputer 22.

Next, operation of the above constructed apparatus will be described hereinafter. The luminous flux emitted from the light sources 1a, 1b, which are alternately turned on, is irradiated on the spot diaphragm 3 through the condenser lens 2. The measuring light passed through the spot diaphragm 3 is condensed at near position from the cornea of the eye 6 and thereafter an image of the spot diaphragm 3 is formed on the fundus. The measuring light reflected from the fundus is reflected by the beam splitter 5 and the reflecting mirror 8 and passed through the cornea reflecting rejection mask 10. Thereby, the fundus image is formed on the light receiving device 14 through the imaging lens 13. On the other hand, the luminous flux, which is emitted from the light source 1a and passed in a region of the visual axis, forms the image of the spot diaphragm 3 onto the fundus on the visual axis. This image of the spot diaphragm 3 becomes a standard position.

The light receiving device 14 detects both the spot diaphragm image by the light source 1a and the spot diaphragm image by the light source 1b, respectively. And based on the detected result by the light receiving device 14, the microcomputer 22 moves the spot diaphragm 3 and the movable lens 12 until the spot diaphragm 3 is positioned at a position conjugated with the fundus of the eye 6 in the meridional direction. Further, the potentiometer 25 detects the moved position of the spot diaphragm 3 as the voltage value and the detected signal of the voltage is input to the microcomputer 22 through the A/D converter 21. The microcomputer 22 conducts calculation processing to convert the positional signal of the spot diaphragm 3 into the refractive power value, thereby the refractive power value in the meridional direction is obtained.

Thereafter, the pulse motor 27 rotates the light source 1b, the cornea reflecting rejection mask 10 and the light receiving device 14 around the optical axis with predetermined steps (for example, steps corresponding to 5 degrees) and the refractive power in the meridional direction from the optical axis is measured. By repeating such operation in succession, the refractive power data can be obtained in all meridional directions of 360 degrees.

Figure 4:
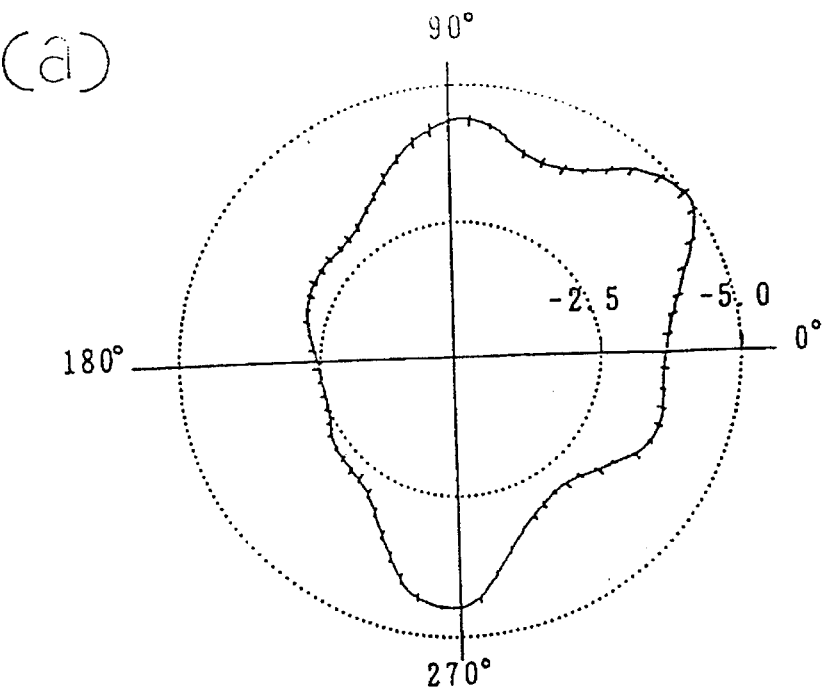
FIG. 4A–4B are views showing a displaying method of the refractive power data of the eye.
Figure 4:
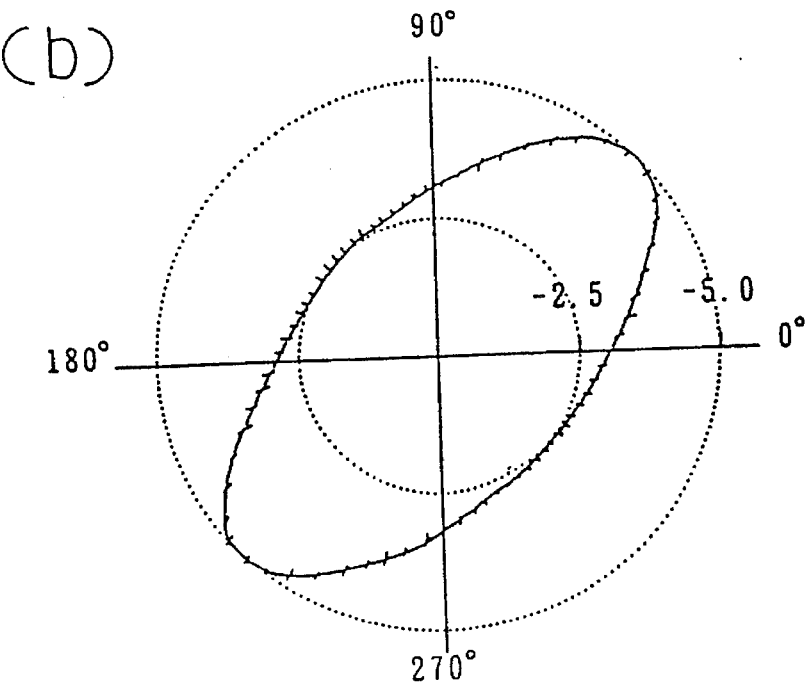

Next, displaying methods by which the thus obtained refractive power data displayed on the display device 28 will be described hereinafter. In FIG. 4, the refractive power data obtained according to the above is plotted corresponding to each of the meridional lines and the distance from the center gives an extent of refractive ametropy. Here, if the distance from the center is long, refractive ametropy is heavy and if the distance from the center is short, refractive ametropy is light. And in order to be able to visually understand, the maximum values of refractive ametropy are plotted on the outer circle and the minimum values thereof are plotted inner circle which has a ½ radius of the outer circle.

For instance, FIG. 4(a) shows the refractive power data obtained from the eye 6 having irregular astigmatism and FIG. 4(b) shows the refractive power data obtained from the eye 6 having simple astigmatism. As shown in FIG. 4 (b), when the ellipse with symmetry is obtained, the spherical refractive power values, the cylindrical refractive power value and the cylindrical axial angle are calculated and displayed on the display device 28.

Figure 5:
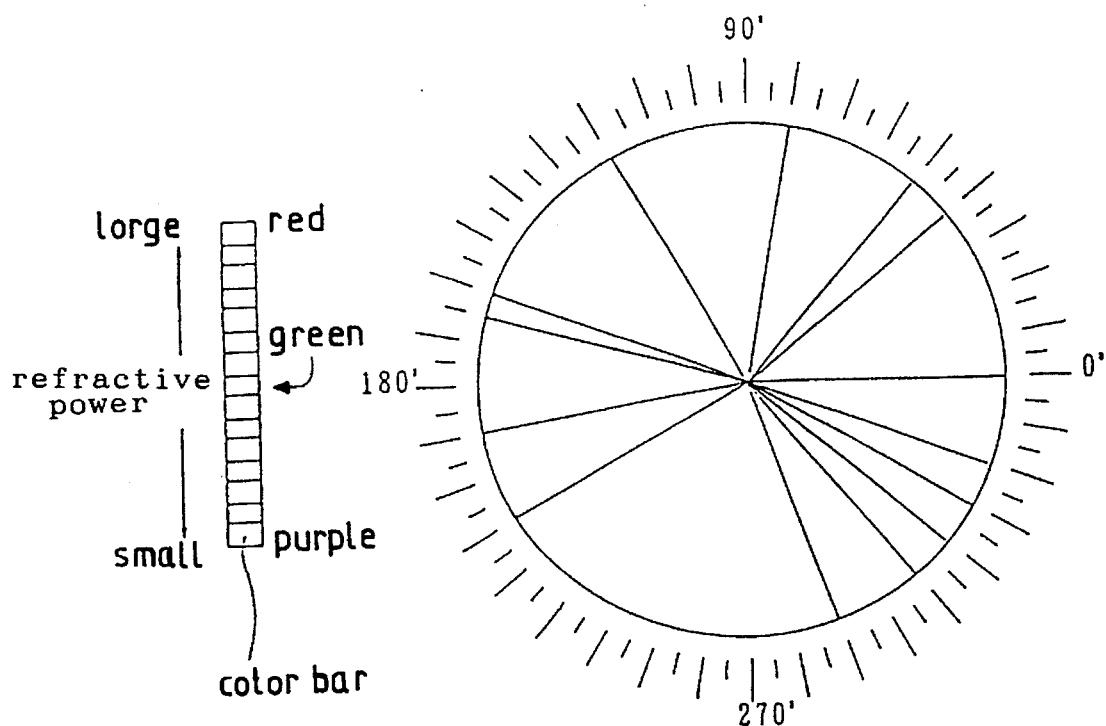
FIG. 5 is a view showing a displaying method in which the refractive power data is graphically displayed according to color graphic.

Further, FIG. 5 shows another displaying method in which the refractive power values are displayed every angle (degrees) in utilizing color classification on the color display. Here, in the color classification, the color is, for instance, classified into 15 stages by combining a hue such as red, orange, yellow, green, blue, indigo blue and purple and a gradation thereof. According to this method, in case that the refractive power in each stage is defined as 0.5 D (diopter), the refractive power values can be relatively displayed in a range of +3.5 D—3.5 D if the spherical equivalent value (SE value) is used as the standard value. And for example, the refractive ametropy may be absolutely displayed based on that hypermetropia is colored in blue direction and myopia is colored in red direction while emmetropia eye is used as the standard point.

Here, though the step for color classification is essentially determined as 0.5 D, it is desirable that changing means is arranged in the apparatus so that such step can be changed. And it will be effective if the graphs in both FIGS. 4 and 5 can be mutually displayed by changing them.

Figure 6:
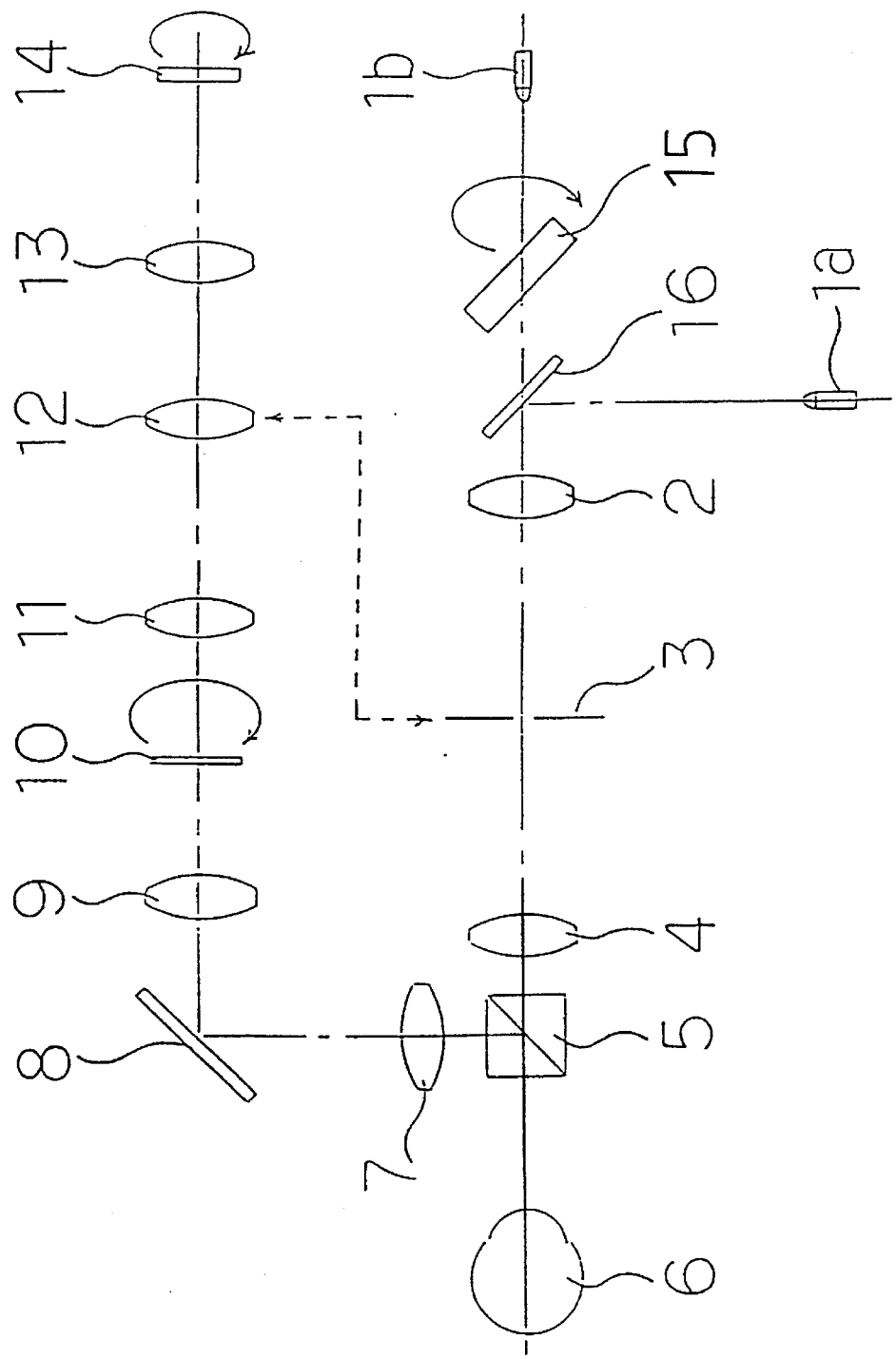
FIG. 6 is a schematic view of the optical system in the second embodiment.

Next, the ophthalmic apparatus of the second embodiment will be given hereinafter, according to FIG. 6. Here, in FIG. 6, the same element as in the first embodiment is indicated by the same numeral. In the second embodiment, the luminous flux from the light source 1b is optically rotated, though in the first embodiment the light source 1b is directly rotated around the optical axis. That is, in the second embodiment, the light source 1b is fixed on the optical axis and a parallel glass 15 is rotatably arranged between the light source 1b and the condenser lens 2. Thereby, the luminous flux emitted from the light source 1b is deviated through the parallel glass 15 and as a result, the same effect in the first embodiment that the light source 1b is positioned distantly from the optical axis can be obtained. And the measuring light source 1a is arranged so that the luminous flux emitted therefrom is reflected by a half-mirror 16 and the main light thereof becomes coaxial with the projecting optical axis.

As mentioned above, in the second embodiment, the parallel glass 15 is rotated around the optical axis synchronous with the cornea reflecting rejection mask 10 and the measuring light receiving device 14, instead that the measuring light source 1b is rotated in the first embodiment.

In addition to the above, the ophthalmic apparatus of the third embodiment will be described according to FIG. 7. Although the refractive power is obtained by projecting the spot target onto the fundus of the eye 6, the refractive power is obtained in the ophthalmic apparatus according to the third embodiment, as follows.

Figure 7:
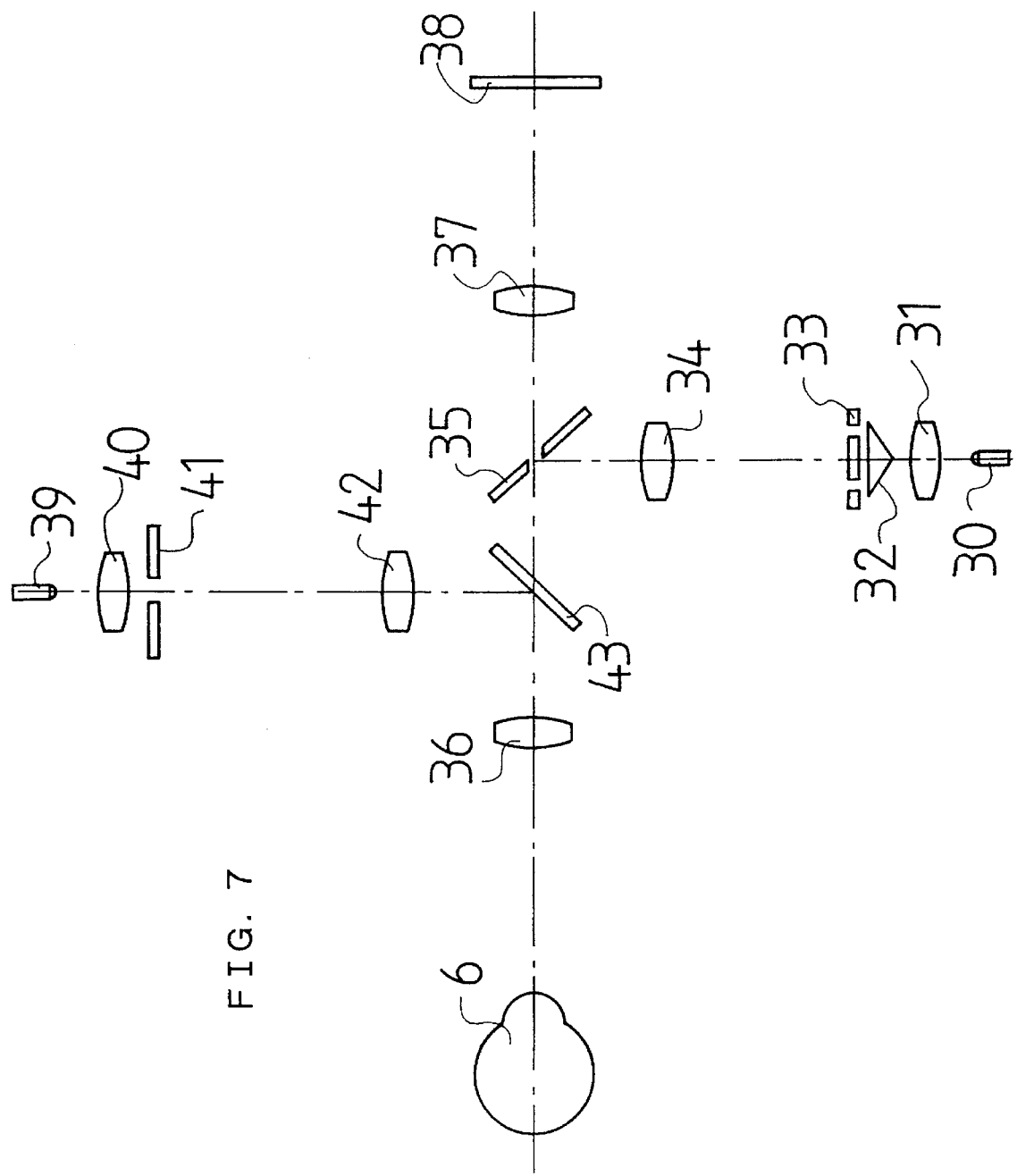
FIG. 7 is a schematic view of the optical system in the third embodiment.

In FIG. 7, numerals 30, 39 indicate infrared light sources which emit infrared rays with a wavelength in the infrared region and numerals 31, 40 indicate condenser lenses. Numeral 32 is a conical prism, numeral 33 is a diaphragm which has a ring hole therein, numeral 41 is a spot diaphragm and numerals 34, 42 are relay lenses. And numeral 35 is a hole mirror having a hole in the center thereof, numeral 43 is a half-mirror, numeral 37 is a imaging lens and numeral 38 is a-two-dimensional image pick-up element such as CCD camera. Here, the diaphragm 33 is arranged at a position conjugated with the fundus of the eye 6 and the spot diaphragm 41 is also arranged at a position conjugated with the fundus of the eye 6. And the fundus is conjugated with the two-dimensional image pick-up element 38. Further, not only both the infrared light source 30 and the hole mirror 35 but also both the hole mirror 35 and the pupil of the eye 6, are mutually arranged with a conjugation relationship therebetween, respectively.

In the above construction, the luminous flux emitted from the infrared light source 30 is irradiated on the diaphragm 33 through the condenser lens 31 and the conical prism 32. The luminous flux passed through the diaphragm 33 is reflected by the hole mirror 35 while passing through the relay lens 34 and thereafter forms an image of the diaphragm 33 onto the fundus of the eye 6 after passing through the objective lens 36. The reflected luminous flux from the fundus is passed through the hole of the hole mirror 35 and forms the fundus image on the element 38 through the imaging lens 37. On the other hand, the luminous flux emitted from the infrared light source 39, which is passed through the region of the visual axis, is reflected by the half-mirror 43 and forms an image of the spot diaphragm 41 onto the fundus on the visual axis.

In the ophthalmic apparatus of the third embodiment, the ring pattern image of the diaphragm 33 is picked up by the element 38 (CCD camera) from the center portion of the eye 6 and the image of the diaphragm 41, which gives the center image of the eye 6, is picked up by the element 38, thereby the refractive power is obtained by calculating the distance between each of the ring patterns and the canter image of the eye 6.

Next, the ophthalmic apparatus according to the fourth embodiment will be described hereinafter. The apparatus is constructed from various systems such as a projection optical system for projecting the measuring target onto the cornea to measure the cornea curvature, a detection optical system for detecting the measuring target to measure the cornea curvature, a projection optical system for projecting the measuring target onto the fundus to measure the eye refractive power, a detection optical system for detecting the measuring target to measure the eye refractive power, a projection optical system for fixation target, an alignment display optical system and a control system. Each system will be described in succession hereinafter.

[Projection Optical System for Measuring Cornea Curvature]

Figure 8:
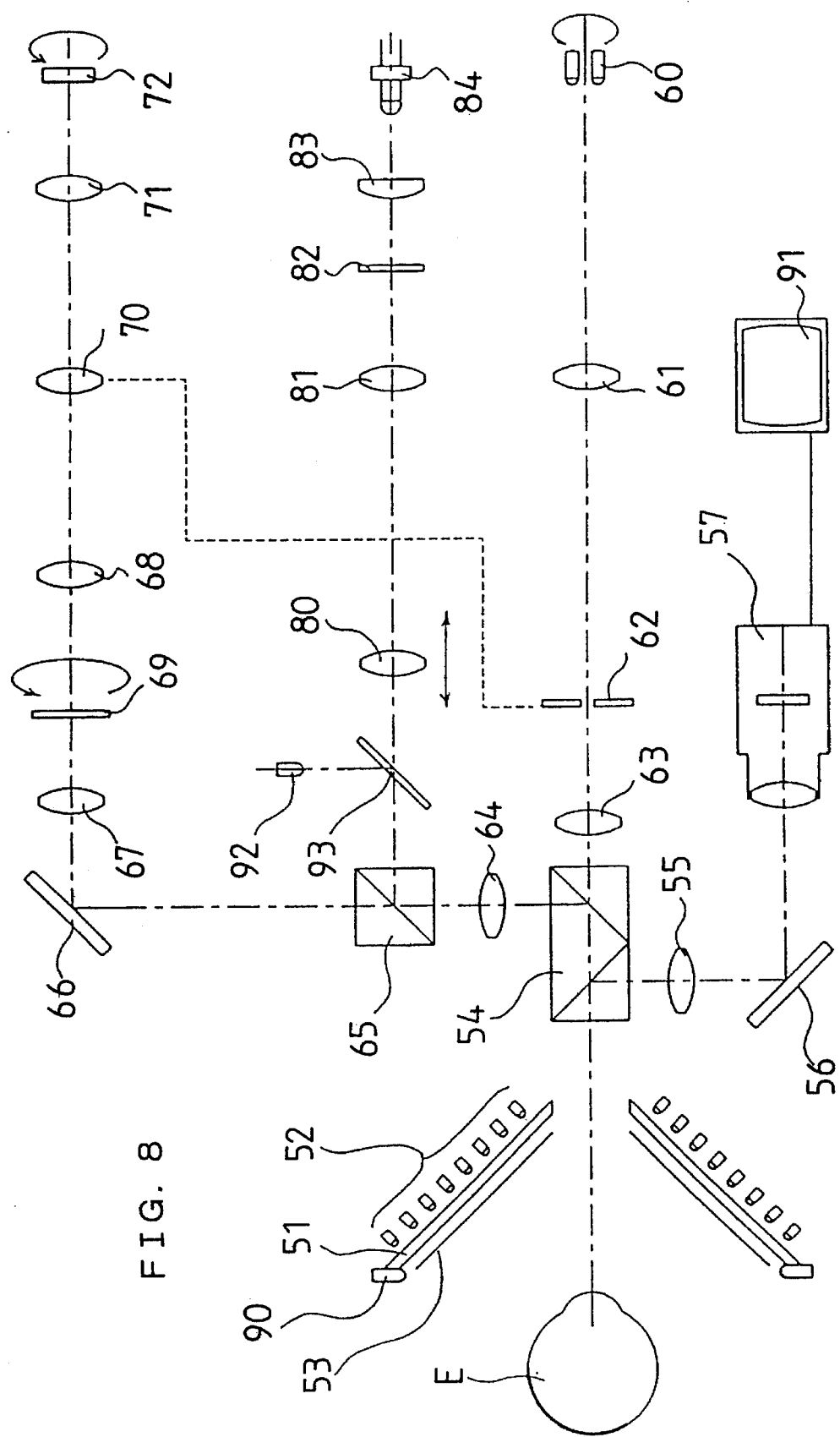
FIG. 8 is a schematic view of the optical system in the fourth embodiment.
Figure 9:
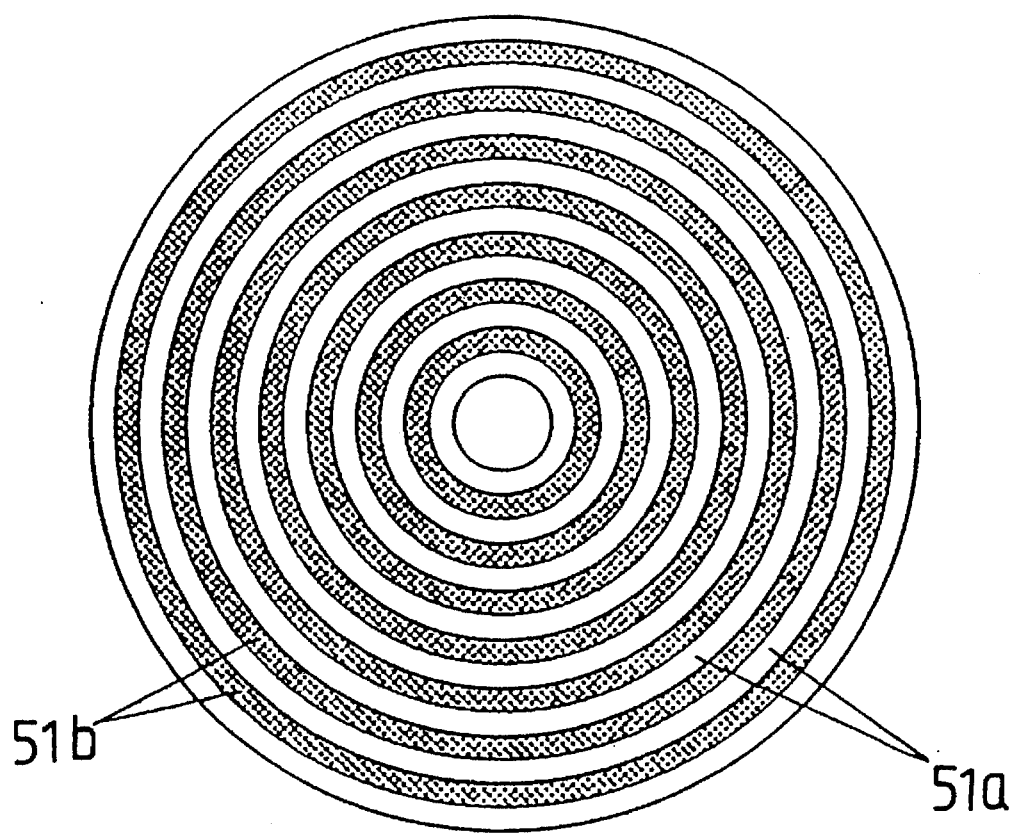
FIG. 9 is a view showing a Placido-plate utilized in the fourth embodiment.

In FIG. 8, numeral 51 is a Placido-plate which has a hole in the center thereof. In the Placido-plate 51, as shown in FIG. 9, a plurality of ring pattern portions 51a through which light can pass, each ring pattern portion 51a having a predetermined width, and a plurality of ring pattern portions 51b by which light is shaded, each ring pattern portion 51b having a predetermined width, are concentrically formed around the optical axis. On the back side of the ring pattern portions 51a, a plurality of light sources 52 such as LED elements by which the ring pattern portions 51a are uniformly irradiated. Each light source 52 emits near infrared rays. The ring pattern formed by irradiating the ring pattern portions 51a through the light sources 52 is projected onto the cornea of the eye E to be examined. At that time, since the front side of the Placido-plate 51 is entirely covered by a film 53 which cuts the visible rays and passes the infrared rays, the person who is examined cannot see the ring pattern.

Here, in the fourth embodiment, as the light sources 52 for irradiating the Placido-plate 51, the light sources emitting near infrared rays are utilized only to avoid miosis of the eye E when the refractive power is measured subsequently. Therefore, as the light sources for irradiating the pattern of the Placido-plate 51, the other light sources emitting red rays can be utilized without being limited to the infrared light sources. And it is conceivable to use a ring fluorescent tube as the light source to irradiate the Placido-plate 51 and to arrange a reflector near the ring fluorescent tube. In this case, the light from the ring fluorescent tube is reflected by the reflector and is irradiated to the pattern of the Placido-plate 51.

[Detection Optical System for Measuring Cornea Curvature]

The reflected light from the cornea which has the ring pattern according to the Placido-plate 51 is reflected through a beam splitter 54 and thereafter forms the cornea reflecting image of the ring pattern on a picture pick-up plane of a CCD camera 57 through a picture pick-up lens 55 and a mirror 56.

[Projection Optical System for Measuring Refractive Power]

Numeral 60 indicates a pair of light sources emitting rays with a wavelength in the near infrared region. The light sources 60 are arranged near a focal point of a condenser lens 61 existing at the side of the light sources 60. In this fourth embodiment, the light sources 60 are symmetrically positioned against the optical axis and are rotated with 180 degrees around the optical axis. However, in order to obtain more detailed information of the refractive power, it is conceivable that one of the light sources 60 is arranged on the optical axis and the other thereof is arranged so as to rotate with 360 degrees around the optical axis. And numeral 82 is a measuring target plate which has a measuring target (spot hole) and is movable so as to set to a position conjugated with the fundus of the eye E. Numeral 63 is a projecting lens and the projecting lens 63 projects the target plate 62 onto the fundus of the eye E.

[Detection Optical System for Measuring Eye refractive Power]

Numeral 64 indicates a objective lens, numeral 65 indicates a beam splitter and numeral 66 indicates a mirror. And numeral 67 and 68 are relay lenses, numeral 69 is a cornea reflecting rejection mask shaped as a band, which is arranged at a position conjugated with the cornea of the eye E, numeral 70 is a movable lens moved synchronously with the target plate 62, numeral 71 is an imaging lens. Numeral 72 is a divided light receiving device which is rotated around the optical axis synchronously with the light sources 60 and the cornea reflecting rejection mask 69.

[Projection Optical System for Fixation Target]

Numeral 80 indicates the first relay lens which is utilized for fogging the eye E by being moved along the optical axis and numeral 81 indicates the second relay lens. And numeral 82 is a fixation target arranged at a focal point of the second relay lens 81, numeral 83 is a condenser lens and numeral 84 is a illumination lamp.

[Alignment Display Optical System]

Numeral 90 is an illumination lamp embedded in the Placido-plate 51, the lamp 90 emitting rays with a wavelength in the near infrared region and irradiating the anterior portion of the eye E. And the lamp 90 is utilized for illuminating the eye E to pick up the anterior image of the eye E. The anterior image of the eye E is picked up by the CCD camera 57 in the above mentioned detection optical system. The image picked up by the CCD camera 57 is displayed on the display device 91. The displayed image is utilized for roughly aligning the optical axis of the apparatus and the eye E.

Numeral 92 is an alignment light source such as LED, the alignment light source 92 emitting rays with a wavelength in the near infrared region. And the alignment light source 92 is arranged to a focal point of the objective lens 64 through the half-mirror 93 and the beam splitter 65 in the projection optical system for fixation target. The light from the alignment light source 92 forms the cornea reflection image and is adjusted to an alignment marker (not shown) for alignment with a predetermined relationship therebetween. The measurement result and the anterior image of the eye E are alternately displayed on the display device 91 by exchanging thereof. As the display device 91, a color liquid crystal display is adopted so as to be able to display color graphics.

[Control System]

Figure 10:
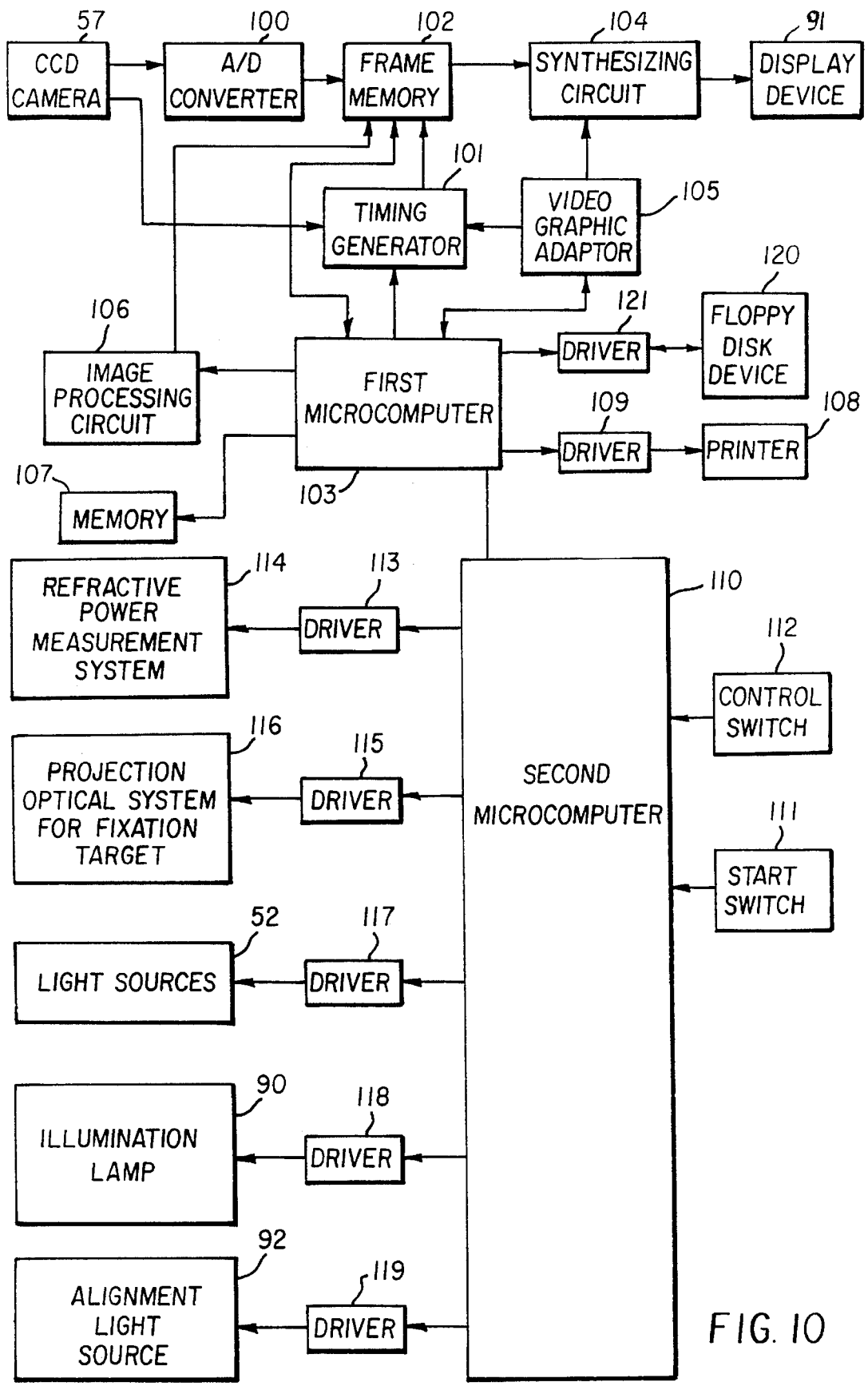
FIG. 10 is an electric block diagram of the fourth embodiment.

The control system of the apparatus will be described with reference to FIG. 10. The signal from the CCD camera 57 is converted to digital signal by a A/D converter 100 and is input to a frame memory 102 synchronous with the clock signal from a timing generator 101. The image data stored in the frame memory 102 is input to a synthesizing circuit 104 under control by the first microcomputer 103 and screened on the display device 91.

To the synthesizing circuit 104, a video graphic adaptor 105 which can form video graphics and characters is connected. The video graphic adaptor 105 displays video graphic images or synthesized images of both the image picked up by a CCD camera 57 and the characters on the display device 91.

Numeral 106 is an image processing circuit which conducts image processing to the Placido-Ring image stored in the frame memory 102 and stores the processing result in a memory 107. Numeral 108 is a printer, numeral 109 is a driver for controlling the printer 108.

And numeral 110 is the second microcomputer connected to the first microcomputer 103. The second microcomputer 110 mainly controls measurement operation. Numeral 111 is a start switch to start measurement, numeral 112 is a control switch having various switches such as a mode exchanging switch for exchanging a cornea shape measurement mode and a refractive power measurement mode. Numeral 113 is a driver for driving a refractive power measurement system 114, numeral 115 is a driver for driving a projection optical system for fixation target 116, numeral 117 is a driver for turning on and off of the light sources 52, numeral 118 is a driver for driving the illumination lamp 90 and numeral 119 is a driver for driving the alignment light source 92. And numeral 120 is a floppy disk device and numeral 121 is a driver for driving the floppy disk device 120.

Figure 11:
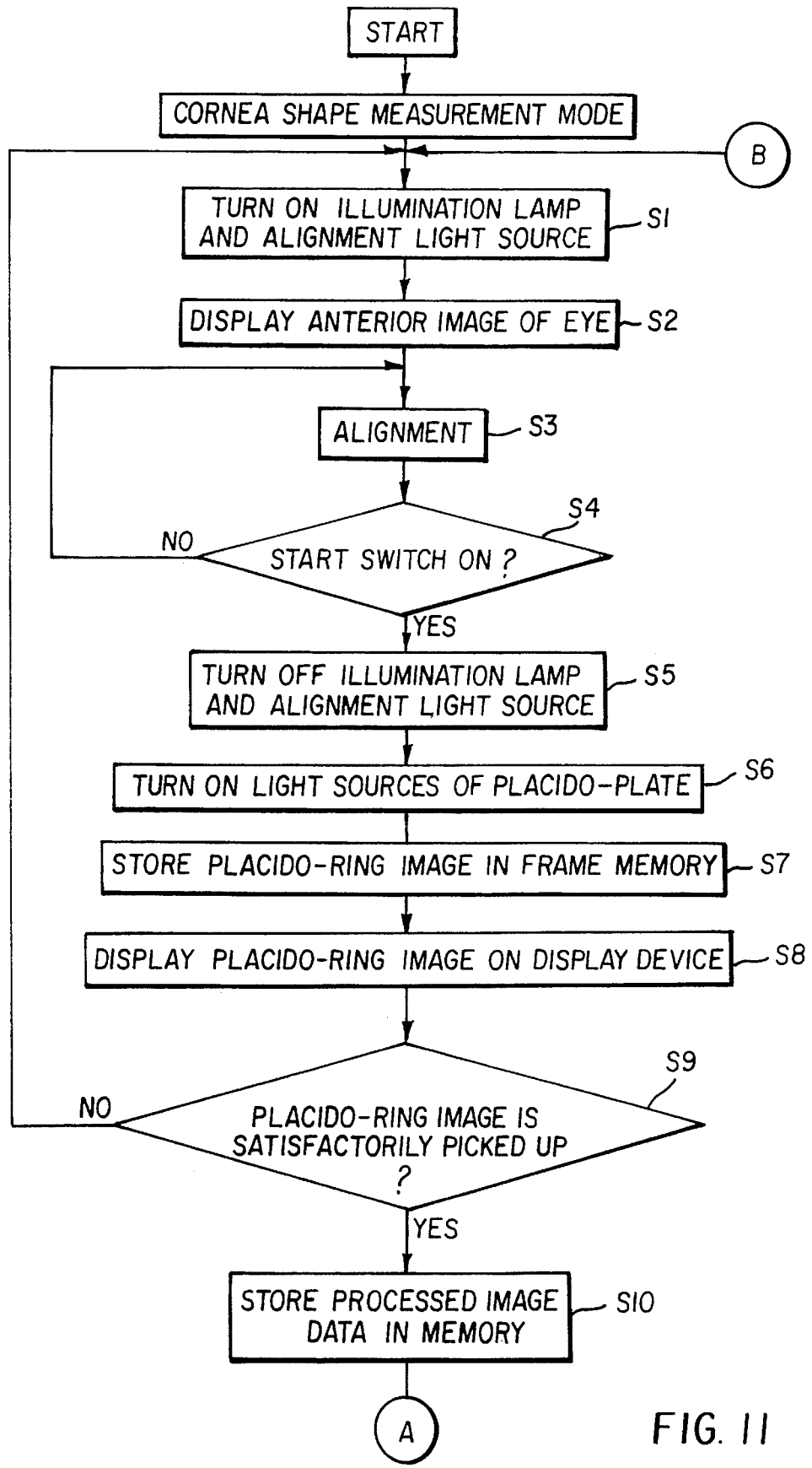
FIG. 11 is a flowchart to explain operation of the fourth embodiment.
Figure 12:
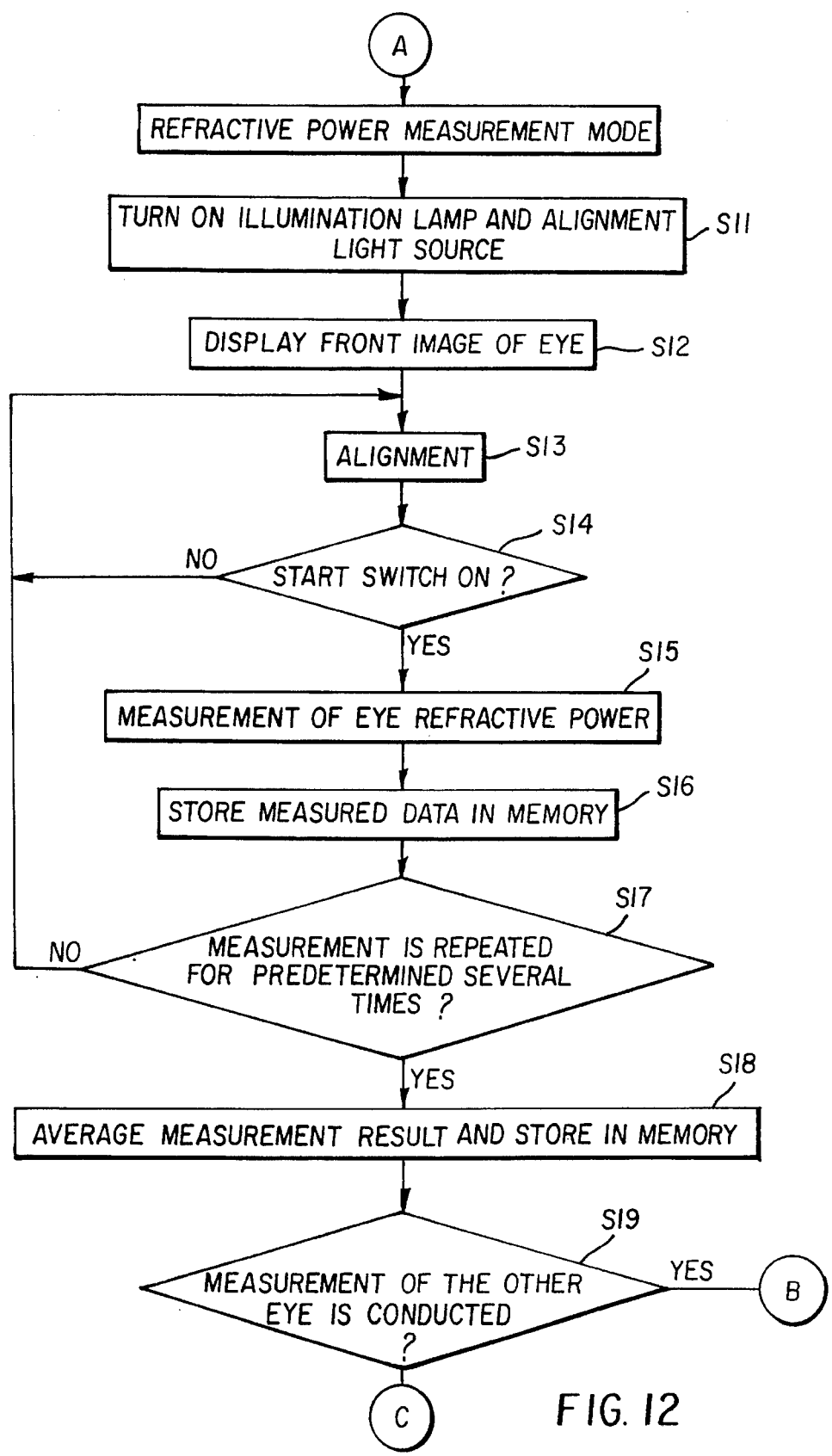
FIG. 12 is a flowchart to explain operation of the fourth embodiment.
Figure 13:
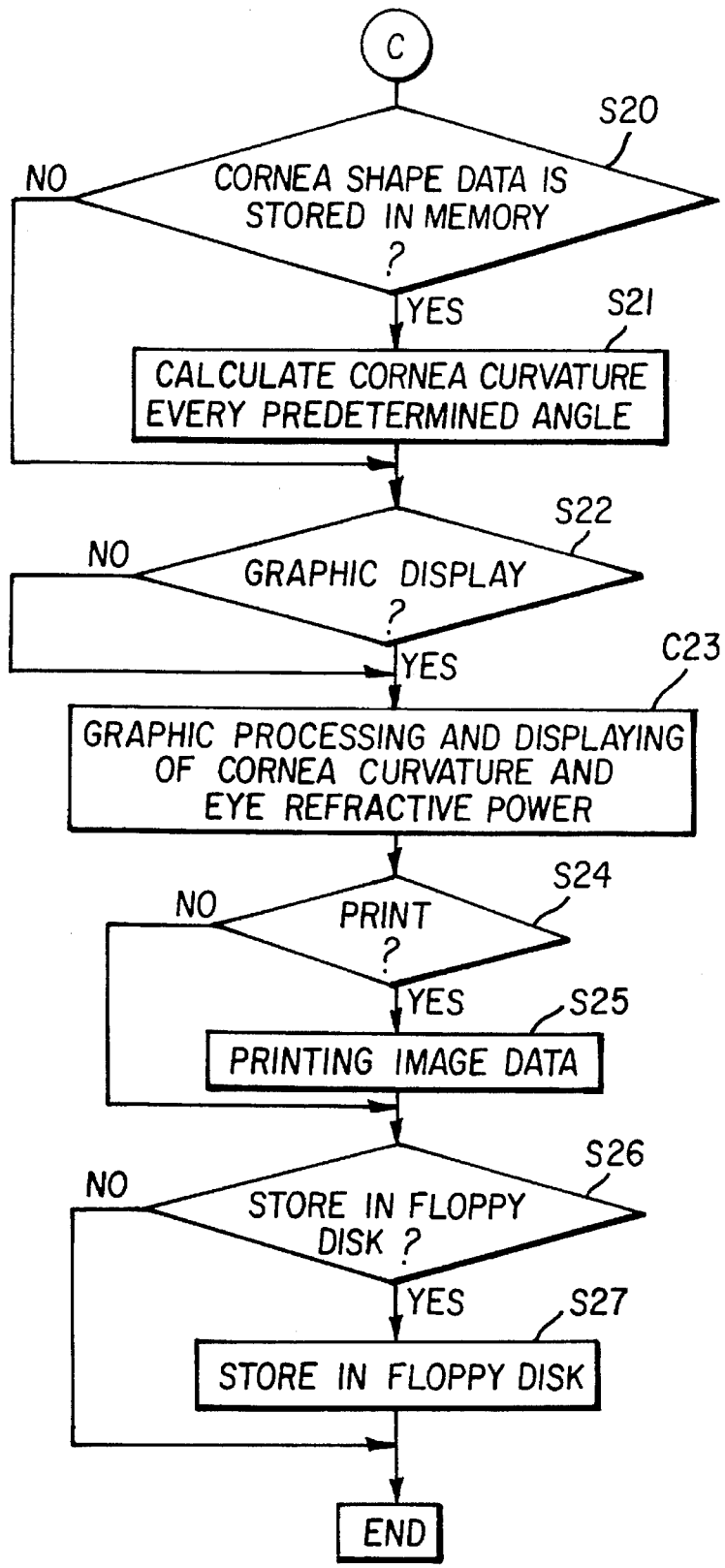
FIG. 13 is a flowchart to explain operation of the fourth embodiment.

Next, operation of the above constructed apparatus will be described with reference to flowcharts in FIGS. 11 to 13. First, the mode exchanging switch in the control switch 112 is selected and the measurement item is determined. Here, operation in a case that a continuous measurement mode where the cornea shape measurement mode and the refractive power measurement mode are successively conducted, will be described hereinafter.

When the continuous measurement mode is selected by the mode exchanging switch, the illumination lamp 90 and the alignment light source 92 are turned on (S1). And the anterior image of the eye E is picked up by the CCD camera 57 and the picked up image is screened on the display device 91 through the frame memory 102 and the synthesizing circuit 104 (S2). The examiner adjusts the anterior image of the eye E, the luminescent point and the alignment mark (not shown) through a well-known sliding mechanism while seeing the display device 91, so that a predetermined relationship is formed among the anterior image of the eye E, the luminescent point and the alignment mark (S3).

And when the start switch 111 is pushed after the alignment is completed (S4; YES), the illumination lamp 90 and the alignment light source 92 are turned off (S5) and the light sources 52 of the Placido-Ring are turned on for a predetermined time interval (S6). Thereby, the Placido-plate 51 is projected on the eye E through the light sources 52 and the Placido-Ring image is formed on the cornea of the eye E.

The Placido-Ring image is picked up by the CCD camera 57 and the image data thereof is stored in the frame memory 102 (S7), thereby the Placido-Ring image is displayed on the display device 91 (S8). At that time, the examiner examines whether the Placido-Ring image displayed on the display device 91 satisfactorily picked up or not. If the image is unsatisfactorily picked up (S9; NO), a cancel switch in the control switch 112 is pushed and the measurement is conducted again (S1). On the contrary, if the image is satisfactorily picked up (S9; YES), a save switch in the control switch 112 is pushed. When the save switch is pushed, the edge detection process is conducted through the image processing circuit 106 and the processed image data is stored in the memory 107 by the first microcomputer 103 (S10).

And at the time that the processed image data is stored in the memory 107, the cornea shape measurement mode is changed to the refractive power measurement mode. First, in this mode, the illumination lamp 90 and the alignment light source 92 are turned on (S11) and the alignment is done by the same procedure as in the cornea shape measurement mode (S12, S13). When the alignment is completed, the start switch 111 is pushed (S14). The second microcomputer 110 operates both the refractive power measurement system 114 and the projection optical system for fixation target 116 based on the signal from the start switch 111.

The measurement light from the light source 60 is passed through the condenser lens 61, the target plate 62 and the projecting lens 63 and is condensed near the cornea of the eye E. Thereafter, the light is reached to the fundus of the eye E. The light reflected on the fundus is passed through the beam splitter 54 and the light path thereof is changed. And the light from the beam splitter 54 is reflected by the mirror 66 and passed through the relay lenses 67, 68. As a result, the light is irradiated on the light receiving device 72 through the imaging lens 71. Further, based on the signal received by the light receiving device 72, the second microcomputer 110 moves both the movable lens 70 and the target plate 62 so that they are arranged at a position conjugated with the fundus of the eye E.

Next, after both the fixation target 82 and the the fundus of the eye E are mutually positioned at the conjugated position through the first relay lens 80, the fixation target 82 is further moved by a suitable diopter so as to fog the eye E. After fogging of the eye E, the light source 60, the cornea reflecting rejection mask 69 and the light receiving device 72 are rotated step by step (for example, every 1 degree) with 180 degrees around the optical axis. While rotating thereof, the target plate 62 and the movable lens 70 are moved according to the signal from the light receiving device 72, thereby the refractive power value in the meridional direction is obtained every rotational step based on quantity of movement of the target plate 62 and the movable lens 70 (S15, S16).

The above measurement of the refractive power is repeated for predetermined several times (S17) and the measurement result is averaged. The averaged data is transmitted to the memory 107 and stored therein (S18). Here, as the measurement data of the refractive power value, the refractive power data in each meridional direction is stored in addition to the spherical refractive power, the cylindrical refractive power and the cylindrical axis. And similar to the above, the measurement of the cornea shape and the refractive power of the other eye E is conducted (S19).

The measurement data of the cornea shape and the refractive power is processed as follows and the displaying data thereof is obtained.

Figure 14:
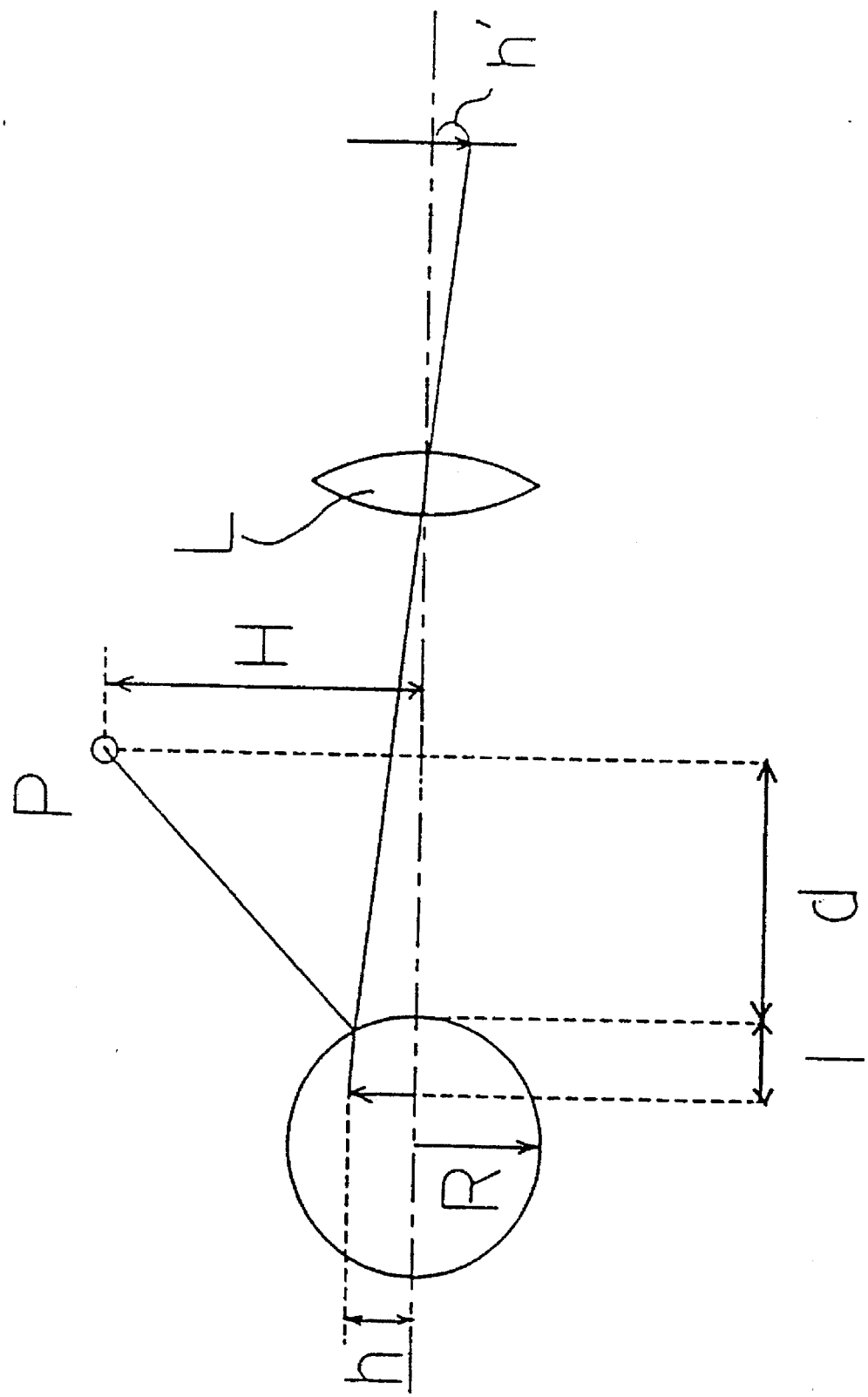
FIG. 14 is a view to explain a calculation method for calculating the cornea curvature.

First, the first microcomputer 103 reads the cornea shape data (S21) and the cornea curvature is calculated every the predetermined angle based on the edge point of each of the rings (S21). Next, calculation method will be described with reference to FIG. 14. In FIG. 14, supposed that the image i of the point light source P, which is located at a position distant from the cornea by the distance d on the optical axis and distant from the optical axis by the height H by the convex cornea, is formed at a position distant from the vertex of the cornea by the distance l and distant from the optical axis by the height h, the equation (1) is materialized.

$$\frac{H}{h} = \frac{d}{l} \quad (1)$$

Next, if the image i is imaged by the lens L on the two dimensional plane, the height is detected as the height h'. Therefore, the magnification m of the optical system in the apparatus is represented by the equation (2).

$$m = \frac{h}{h'} \quad (2)$$

Here, if the curvature radius of the cornea is R, the focal length f of the cornea as the convex mirror is represented by the equation (3).

$$f = \frac{R}{2} \quad (3)$$

And if it exists a relationship according to the equation (4) between the focal length f and the distance d, a relationship between the distance l and the focal length f is represented by the equation (5).

$$f \ll d \quad (4)$$

$$l \approx f \quad (5)$$

Thus, according to the equations (2), (3) and (5), the equation (1) is rewritten into the equation (6).

$$\frac{H}{m \cdot h'} = \frac{2d}{R} \quad (6)$$

By modifying the equation (6), the equation (7) is obtained.

$$R = \frac{2d}{H} \cdot mh' \quad (7)$$

That is to say, the distance d, the height H and the magnification m are inherent values for the apparatus. Therefore, if the height h' is obtained, the curvature radius R of the cornea in the region where the image is observed can be obtained.

Here, in case that the curvature radius of the cornea in the small region is calculated, for example, every one degree in the meridional direction against light and shade edges of each Placido-Ring according to the above equations, it is necessary to calculate for several thousands points. As a result, the processing time becomes longer. In order to avoid this problem, it is conceivable to use the following calculation method to calculate the curvature radius R of the cornea.

Here, supposed that the curvature in the region where the $j_{th}$ ring is projected is defined as the curvature radius $R_j$, the constant determined by the height of the jth ring, the distance to the eye and the image magnification in the apparatus is $K_j$ and the image height on the screen is $h_j$, the above equations are simply represented as the equation (8).

$$R_j = k_j \cdot h_j \quad (8)$$

In the equation (8), the constant $K_j$ can be obtained as the inherent value of the apparatus by beforehand measuring a plurality of the spherical eye models, each having the known curvature, which cover the measurement range of the apparatus. The thus obtained constant $K_j$ is stored in the non-volatile memory of the apparatus. And when the curvature radius of the eye is measured, the curvature can be easily and quickly calculated by reading the constant $K_j$ from the non-volatile memory and calculating the curvature radius according to the equation (8). Further, at this time, manufacturing error of the apparatus can be corrected.

By conducting the above calculation, the cornea curvature is obtained every the predetermined angle at edge in each ring image. The obtained cornea curvature is stored. Here, the calculation process of the cornea curvature is conducted by the first microcomputer 103, and thus while such processing by the first microcomputer 103, it is conceivable that the eye refractive power is measured by the second microcomputer 110.

The cornea curvature data and the eye refractive power data which are obtained according to the above, are displayed on the display device 91 (S22). At that time, display contents can be selected by the switch in the control switch 112.

Figure 15:
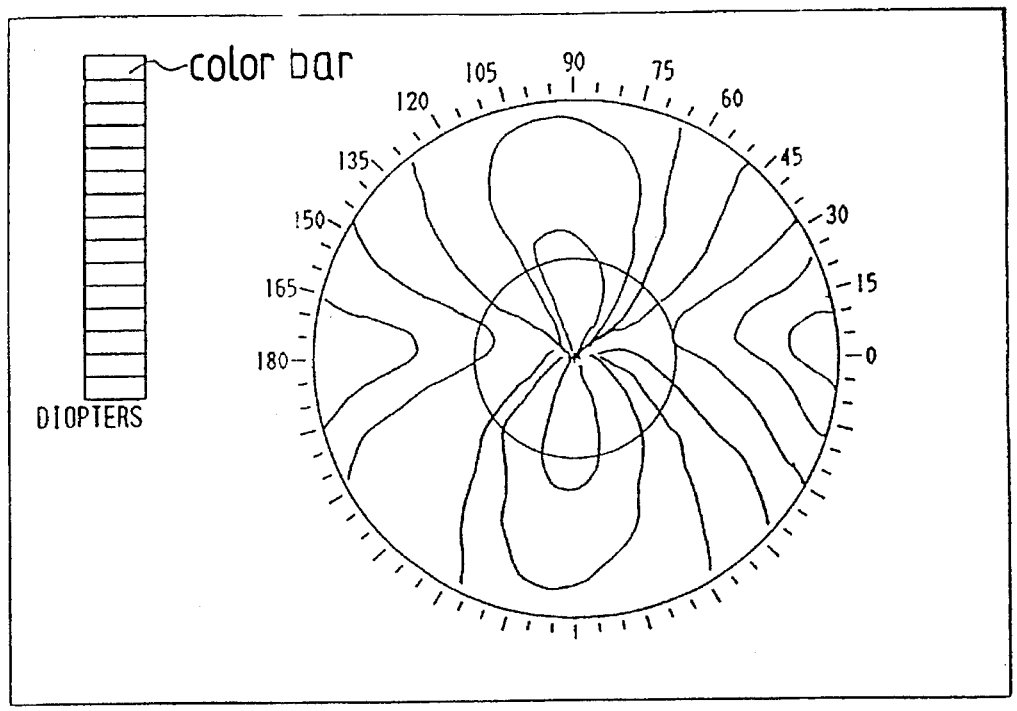
FIG. 15 is a graph in which the distribution of the cornea refractive power is graphed in using a color map.

Next, the display contents about the cornea curvature data and the eye refractive power data will be described with reference to FIGS. 15 and 16. FIG. 15 shows a display example using color map by converting the curvature radius of the cornea into the corneal refractive power through a well-known calculating method and classifying the distribution thereof in each color (S23). In such color classification, the color is, for instance, classified into 15 stages by combining a hue such as red, orange, yellow, green, blue, indigo blue and purple and a gradation thereof, and the red shows the maximum refractive power, the purple shows the minimum refractive power. According to this, the refractive power value between the maximum refractive power and the minimum refractive power is divided into 15 stages and each stage of the color classification (15 stages) is corresponded to each refractive power value. In FIG. 15, the inner circle in the color map is displayed so that the circle is superposed over the pupil position of the eye.

Figure 16:
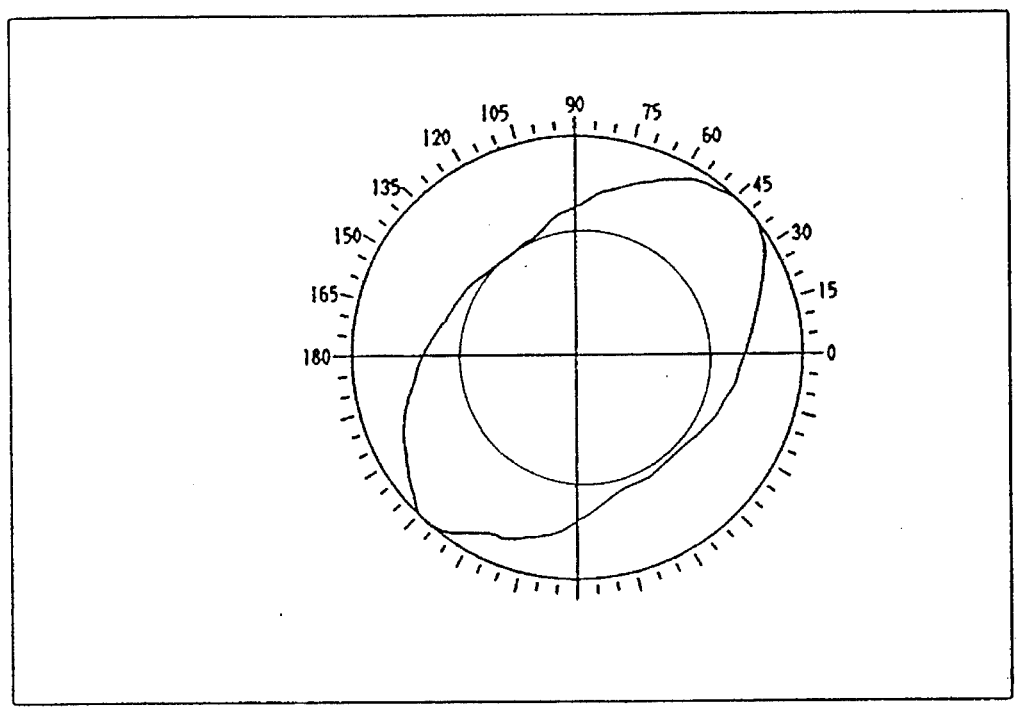
FIG. 16 is a graph in which the measured data of the eye refractive power is plotted therein.

FIG. 16 shows a graph in which the eye refractive power data is plotted corresponding to each meridional line. In FIG. 16, the extent of the refractive ametropy is indicated by the distance from the center. And in order to visually understand, the maximum value of the refractive ametropy is plotted on the outer circle and the minimum value of the refractive ametropy is plotted on the inner circle which has a ½ radius of the outer circle (S23).

Figure 17:
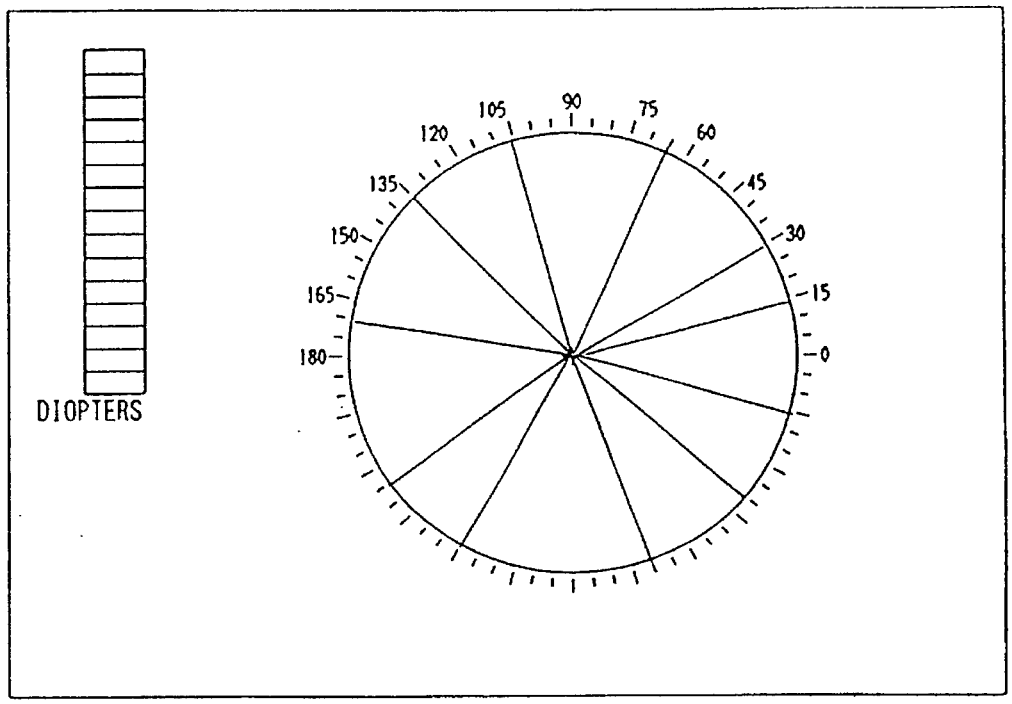
FIG. 17 is a graph in which the measured data of the eye refractive power is graphed in using a color map.

FIG. 17 shows an example of color map in which the refractive power data is indicated corresponding to each angle. The color classification is conducted in 15 stages as in the case of FIG. 15. According to this method, in case that the refractive power in each stage is defined as 0.5 D (diopter), the refractive power values can be relatively displayed in a range of +3.5 D—3.5 D if the spherical equivalent value (SE value) is used as the standard value (S23). And for example, the refractive ametropy may be absolutely displayed based on that hypermetropia is colored in blue direction and myopia is colored in red direction while emmetropia eye is used as the standard point.

Figure 18:
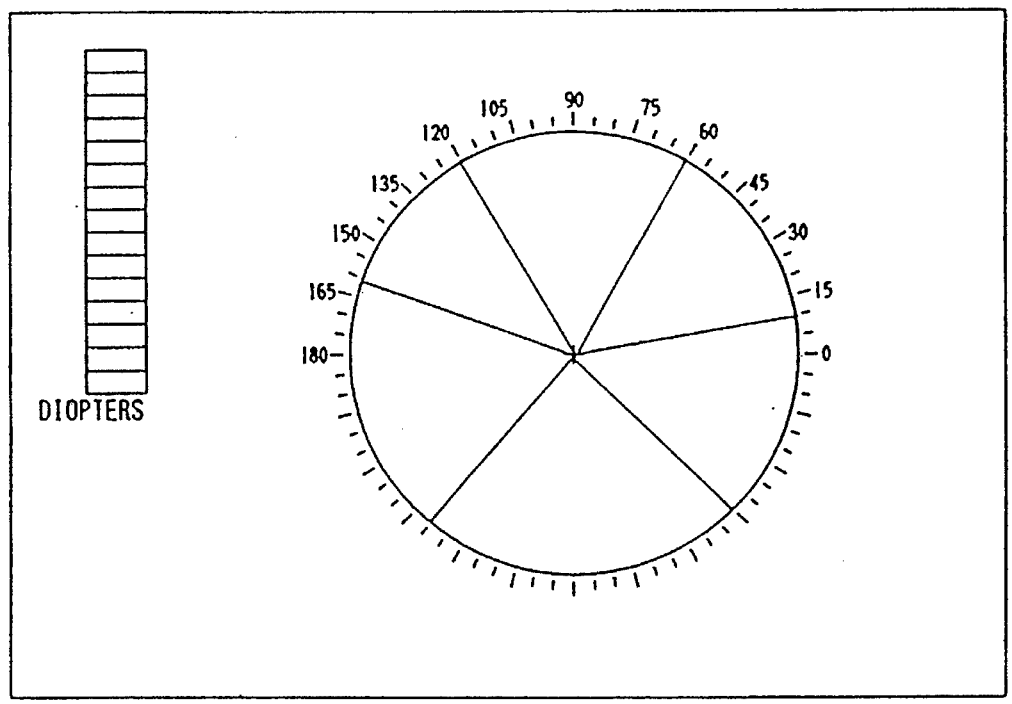
FIG. 18 is a graph in which remaining astigmatism is graphed in using color map.

Next, a method to display the remaining astigmatism based on the cornea curvature data and the eye refractive power data will be described referring to FIG. 18. FIG. 18 shows an example of color map in which the remaining astigmatism (defined by the difference between the total astigmatism and the cornea astigmatism) calculated based on the cornea refractive power data derived from the cornea refractive power data in the pupil area as shown in FIG. 15 corresponding to each measurement region and the eye refractive power data (the data converted to the refractive power when the vertex of the cornea is selected as the standard). In FIG. 18, the same color classification as in the FIG. 17 may be conducted (S23). Here, the total astigmatism substantially equals to sum of the cornea astigmatism and the astigmatism in the crystalline lens. Thus, the data obtained based on the cornea curvature data (the cornea refractive power data) and the eye refractive power data may be effectively used for correction of the cornea in the refractive ametropy. Further, in addition for the cornea correction, the above data will be effectively used in a case that a silicon gel type IOL (Intra Ocular Lens) by which the focal point is changeable is practiced instead of the intraocular lens implant which has a fixed focal point.

Here, as in the first embodiment, it is conceivable that one of the light sources 60 is arranged on the optical axis and the other is arranged so as to rotate 360 degrees around the optical axis, thereby the refractive power is obtained in all directions of 360 degrees. In this case, the color map display of the cornea refractive power can be more suitably conducted. Such construction will be omitted since it is apparent from FIG. 1. The display data is printed by the printer 108 through the driver 109 if necessary (S24, S25) and is stored in the floppy disk device 120 through the driver 121 if necessary (S26, S27).

Next, the fifth embodiment will be described hereinafter with reference to FIG. 19. Here, in FIG. 19, the same elements in the aforementioned fourth embodiment is numbered by the same numbers.

In the fourth embodiment, the light path through which the luminous flux of the target for measuring the eye refractive power is secured in the Placido-plate 51 by opening the hole in the center of the Placido-plate 51. However, in this case, more information about the cornea shape in the center of the cornea cannot be obtained. In order to improve this point, measurement of the cornea curvature in the cornea center can be done in the fifth embodiment.

Figure 19:
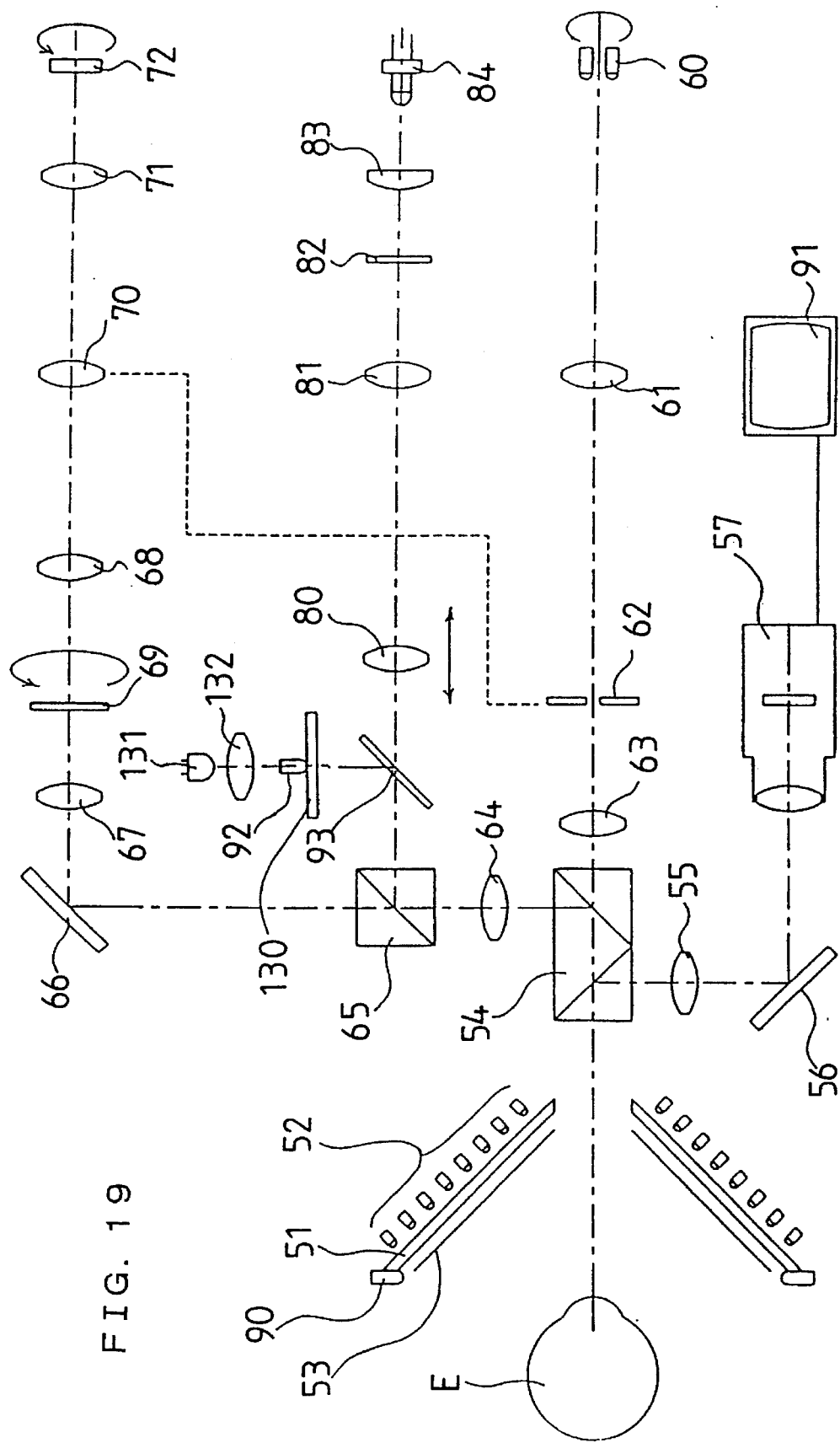
FIG. 19 is a schematic view of the optical system in the fifth embodiment.

In FIG. 19, numeral 130 is the second plane Placido-plate arranged at the focal point of the objective lens 64 and on the upper surface of the second Placido-plate 130, transparent portions which is able to pass light are formed at the center and concentrically in a form of plurality of ring patterns, and further light shading portions are concentrically formed in a form of plurality of ring patterns.

Numeral 131 is the second illumination light for illuminating the second Placido-plate 130, the illumination light 131 emitting rays in near infrared region. The second illumination light 131 uniformly irradiates the second Placido-plate 130 through a condenser lens 132 and projects the ring pattern image onto the cornea of the eye E through the objective lens 64.

Here, if the focal length of the objective lens 64 is $f_1$, the image formed by the cornea having the curvature radius R is formed at the focal point of the objective lens 64 with a size of $(R/2)/f_1$. According to this, the distribution of the cornea curvature can be obtained by detecting the ring pattern image on the plane that the image is picked up and conducting calculation process as in the fourth embodiment.

As mentioned above, in the apparatus of the fifth embodiment the detailed information about the cornea center region can be obtained, therefore such apparatus would be very useful for operation to correct the refractive ametropy in which it is necessary to know the information about the cornea center region.

While the invention has been particularly shown and described with reference to preferred embodiments thereof, it will be understood by those skilled in the art that the foregoing and other changes in form and details can be made therein without departing from the spirit and scope of the invention.

What is claimed is:

1. An ophthalmic apparatus for measuring characteristic of an eye to be measured, the ophthalmic apparatus comprising:

projection means for projecting a target onto a fundus of the eye in many meridional directions in a cornea of the eye so as to substantially cover all over the cornea in substantially all meridional directions of 360 degrees;

detecting means for detecting a position of a target image projected onto the fundus by the projection means;

calculation means for calculating refractive power values in the meridional directions based on a detected result through the detection means; and display means for graphically displaying distribution of the refractive power values calculated by the calculation means.

2. The ophthalmic apparatus according to claim 1, wherein the projection means comprises;

first projection means for projecting a first target on a visual axis of the cornea;

second projection means for projecting a second target out of the visual axis of the cornea;

wherein the calculation means calculates the refractive power values in the meridional directions based on a distance between a first target image projected by the first projection means and a second target image projected by the second projection means.

3. The ophthalmic apparatus according to claim 1, wherein the projection means comprises;

a target plate having a hole on an optical axis of an optical system in the apparatus;

a first light source for irradiating the target plate, the first light source being arranged on the optical axis;

a second light source for irradiating the target plate, the second light source being arranged out of the optical axis; and rotation means for rotating luminous flux emitted from the second light source around the optical axis.

4. The ophthalmic apparatus according to claim 1, wherein the display means displays the distribution of the refractive power values as curves which are formed by connecting points corresponding to the refractive power values on meridional lines in the meridional directions.

5. The ophthalmic apparatus according to claim 1, wherein the display means displays the distribution of the refractive power values by mutually coloring each of the refractive power values in a different color.

6. An ophthalmic apparatus for measuring characteristics of an eye to be measured, the ophthalmic apparatus comprising:

position adjusting means for aligning an optical system in the apparatus in a predetermined relationship against the eye;

first projection means for projecting a first target having many ring patterns onto a cornea of the eye so as to measure a cornea shape;

first pick up means for picking up the first target projected by the first projection means;

image process means for extracting an image of the first target by processing a first target picked up through the first pick up means;

cornea shape calculation means for calculating a shape of each section of the cornea based on a position of the image of the first target;

second projection means for projecting a second target onto a fundus of the eye in a plurality of meridional directions so as to measure refractive power values in substantially all meridional directions of 360 degrees;

light detection means for detecting a second target image projected by the second projection means;

refractive power calculation means for calculating the refractive power values based on a detected result through the light detection means;

mode exchanging means for exchanging a cornea shape measurement mode and a refractive power measurement mode; and display means for displaying the measured cornea shape and the measured refactive power.

7. The ophthalmic apparatus according to claim 6, wherein the position adjusting means comprises;

illumination means for illuminating an anterior portion of the eye;

third projection means for projecting a third target on the eye so as to align the optical system through the position adjusting means;

wherein the front portion of the eye is picked up by the first pick up means and an image of the front portion is displayed by the display means.

8. The ophthalmic apparatus according to claim 7, wherein both the illumination means and the third projection means have light sources.

9. The ophthalmic apparatus according to claim 8, further comprising control means for turning off the light sources of the illumination means and the third projection means based on a measurement start signal in the cornea shape measurement mode.

10. The ophthalmic apparatus according to claim 6, wherein the second projection means projects the second target onto the fundus of the eye in the meridional directions so as to substantially cover all over the cornea and the refractive power calculation means calculates the refractive power values in each of the meridional directions.

11. The ophthalmic apparatus according to claim 10, further comprising remaining astigmatism calculation means for calculating a remaining astigmatism based on the refractive power values in each of the meridional directions and the cornea shape calculated by the cornea shape calculation means.

12. The ophthalmic apparatus according to claim 6, wherein the first projection means comprises;

center target projection means for projecting a center target to a center area of the cornea;

peripheral target projection means for projecting a peripheral target to a peripheral area of the cornea.

13. An ophthalmic apparatus for measuring characteristics of an eye to be measured, the ophthalmic apparatus comprising:

position adjusting means for aligning an optical system in the apparatus in a predetermined relationship against the eye;

first projection means for projecting a first target having a plurality of ring patterns onto a cornea of the eye so as to measure a cornea shape;

first pick up means for picking up the first target projected by the first projection means;

image process means for extracting an image of the first target by processing a first target picked up through the first pick up means;

cornea shape calculation means for calculating the cornea shape based on a position of the image of the first target;

second projection means for projecting a second target onto a fundus of the eye in a plurality of meridional directions so as to measure refractive power values;

light detection means for detecting a second target image projected by the second projection means;

refractive power calculation means for calculating the refractive power values based on a detected result through the light detection means;

mode exchanging means for exchanging a cornea shape measurement mode and a refractive power measurement mode; and display means for displaying the measured cornea shape and the measured refractive power;

wherein the second projection means projects the second target onto the fundus of the eye in the meridional directions so as to substantially cover all over the cornea and the refractive power calculation means calculates the refractive power values in each of the meridional directions;

wherein the second projection means comprises center target projection means for projecting a center target onto the fundus of the eye on a visual axis of the cornea, and peripheral target projection means for projecting a peripheral target around the center target out of the visual axis of the cornea; and wherein the refractive power calculation means calculates the refractive power values in the meridional directions based on a distance between a clear target image and a peripheral target image.

14. An ophthalmic apparatus for measuring characteristics of an eve to be measured, the ophthalmic apparatus comprising:

position adjusting means for aligning an optical system in the apparatus in a predetermined relationship against the eye;

first projection means for projecting a first target having a plurality of ring patterns onto a cornea of the eye so as to measure a cornea shape;

first pick up means for picking up the first target projected by the first projection means;

image process means for extracting an image of the first target by processing a first target picked up through the first pick up means;

cornea shape calculation means for calculating the cornea shape based on a position of the image of the first target;

second projection means for projecting a second target onto a fundus of the eye in a plurality of meridional directions so as to measure refractive power values;

light detection means for detecting a second target image projected by the second projection means;

refractive power calculation means for calculating the refractive power values based on a detected result through the light detection means;

mode exchanging means for exchanging a cornea shape measurement mode and a refractive power measurement mode; and display means for displaying the measured cornea shape and the measured refractive power;

wherein the second projection means comprises center target projection means for projecting a center target onto the fundus of the eye on a visual axis of the cornea, and peripheral target projection means for projecting a peripheral target around the center target out of the visual axis of the cornea.

* * * * *